United States Patent [19]
Rassoli et al.

[11] Patent Number: 5,662,473
[45] Date of Patent: Sep. 2, 1997

[54] ADJUSTABLE-ANGULATION PATTERN FOR MAKING A DENTAL-IMPLANT ABUTMENT

[75] Inventors: Kazem Rassoli, Anaheim, Calif.; James G. Ironside, Sydney, Australia

[73] Assignee: Vident, Brea, Calif.

[21] Appl. No.: 528,480

[22] Filed: Sep. 14, 1995

Related U.S. Application Data

[63] Continuation-in-part of Ser. No. 162,662, Dec. 2, 1993, abandoned.

[51] Int. Cl.$^6$ ............ A61C 13/12; A61C 13/225; A61C 8/00
[52] U.S. Cl. ............................................. 433/172; 433/173
[58] Field of Search .................... 433/172, 173, 433/174, 175, 176, 214

[56] References Cited

U.S. PATENT DOCUMENTS

| | | | |
|---|---|---|---|
| 4,852,872 | 8/1989 | Detsch | 433/173 |
| 5,106,300 | 4/1992 | Voitik | 433/173 |
| 5,125,841 | 6/1992 | Carlsson et al. | 433/172 X |
| 5,135,395 | 8/1992 | Marlin | 433/173 X |
| 5,154,612 | 10/1992 | Carlsson et al. | 433/173 |
| 5,259,759 | 11/1993 | Jorneus et al. | 433/173 |

FOREIGN PATENT DOCUMENTS

| 2669210 | 5/1992 | France | 433/174 |
|---|---|---|---|

*Primary Examiner*—Nicholas D. Lucchesi
*Attorney, Agent, or Firm*—Christie, Parker & Hale, LLP

[57] ABSTRACT

A dental system including a precision base and an abutment pattern for making a cast custom abutment for attachment to a dental implant body in a patient's jawbone. The base is made of a cast-to metal such as a gold alloy, and the abutment pattern is made of a burn-out material such as plastic. Wax may be added to the pattern for shape augmentation, and the pattern may also be machined for shape reduction. The pattern has a tapered post which is angulated with respect to a central axis of the base, thereby enabling construction of an angulated abutment which corrects for imperfect placement of the implant body in the jawbone.

12 Claims, 3 Drawing Sheets

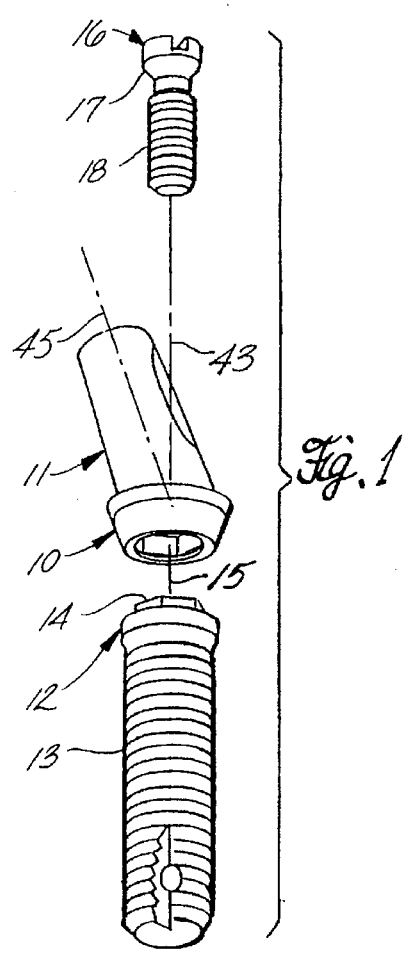
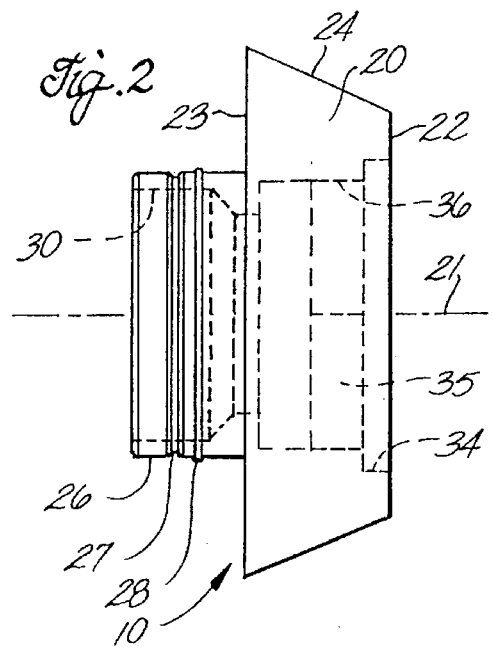
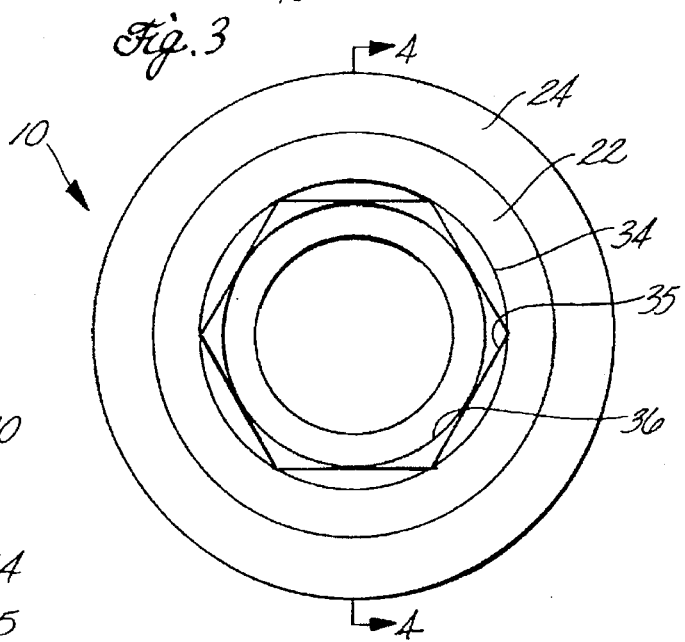
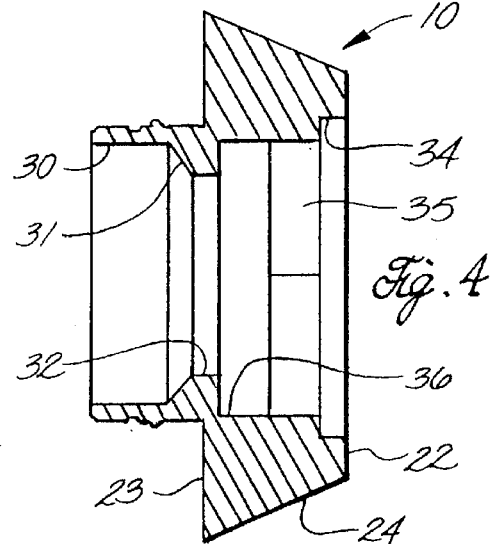

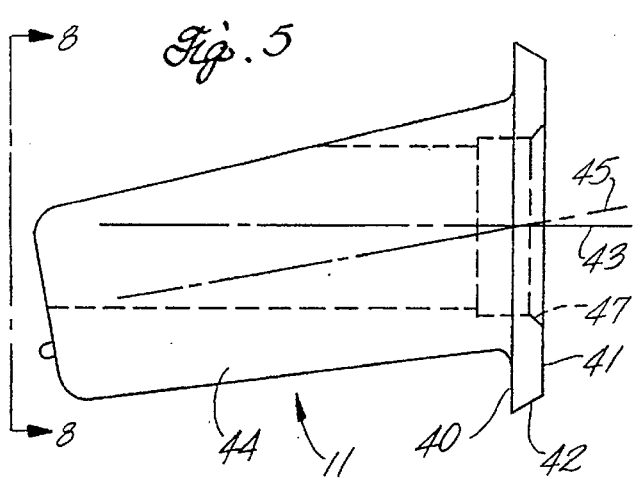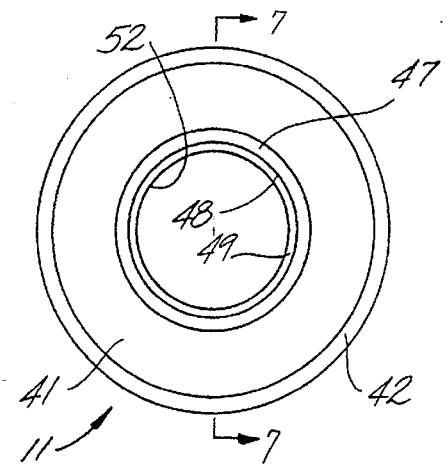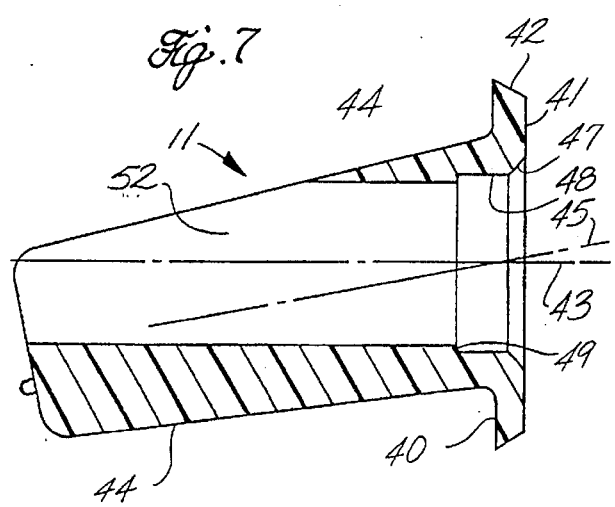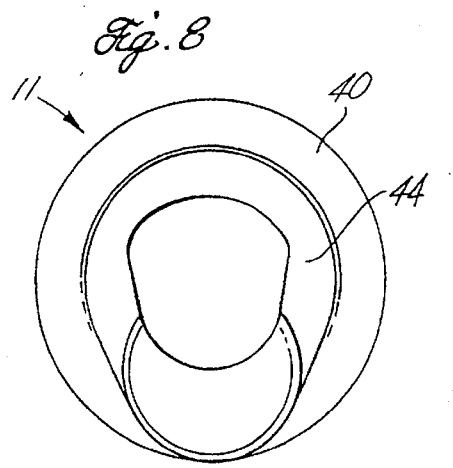

ADJUSTABLE-ANGULATION PATTERN FOR MAKING A DENTAL-IMPLANT ABUTMENT

CROSS REFERENCE TO RELATED APPLICATION

This application is a continuation in part of U.S. patent application Ser. No. 08/162,662 filed Dec. 2, 1993, now abandoned.

BACKGROUND OF THE INVENTION

Prosthodontics is the specialized branch of dentistry which deals with repair or replacement of damaged or missing teeth which are lost due to poor dental hygiene, disease or injury. Replacement of missing teeth is important to provide proper mastication and speech, to avoid over-stressing or unwanted movement of remaining natural teeth, and to maintain good facial appearance.

A fundamental problem in restorative dentistry is the method of attachment or anchorage of the artificial tooth or teeth. Historically, fixed or removable appliances supporting the artificial tooth or teeth have relied on attachment to adjacent natural teeth, and this anchorage method typically involves some unwanted removal of structure of the adjacent natural teeth to provide attachment sites. In the more difficult case of a patient with no remaining natural teeth in one or both of the upper and lower dental arches, complete dentures are constructed to fit over the ridge of gum tissue which overlies the supporting upper or lower jawbone. Anchorage of a complete denture is imperfect, and frequently a source of discomfort and annoyance to the patient.

In recent years, dental implant bodies have been developed to provide a greatly improved solution to the problem of anchoring a single artificial tooth or an appliance supporting two or more artificial teeth. An implant body is typically a metal body of cylindrical shape which is threaded or otherwise fitted into a mating hole drilled in the jawbone in a surgical installation procedure.

Implant bodies are usually made of titanium which is both strong and biocompatible with the bone. Apertures or irregular surfaces may be provided on the implant-body exterior, or alternatively the exterior may be coated with hydroxyapatite to encourage bone growth around and into the implant body for increased anchorage during the healing process which may take from two or three up to six months. After surgical implantation and during the healing process, the overlying gum tissue may be closed over the gingival facing end of the implant body.

When the healing period is over, and the implant body is firmly secured in the jawbone by a process called osseointegration, the gum tissue is incised to expose the gingival end of the implant body which is provided with a threaded socket (or alternatively, a threaded post) or similar attachment site. A transmucosal healing cap is installed in the incision and screwed into the implant body. The patient is then referred to the restoring dentist, and a superstructure called an impression post is secured to the attachment site to extend transmucosally through the gum tissue into the space where an artificial tooth or multiple-tooth appliance is to be mounted.

A conventional impression is then taken of the dental arch, with the impression post in place to form a socket in the impression material. When the hardened impression material is removed from the mouth, the post is removed from the implant body, and placed in the impression socket. An implant analog (a metal body generally corresponding in shape to the now-embedded implant body in the patient's jawbone) is threaded on the post end which extends from the impression, and a conventional stone (dental plaster) model is then poured in the impression. The stone model reproduces the contours of the patient's teeth and gums, and the implant analog is positioned within the stone model in the exact position of the implant body embedded in the jawbone.

A dental-laboratory technician then removes the impression post, and attaches a tapered biocompatible post called an abutment to the implant analog. The abutment will later be attached to the implant body in the patient's jawbone to provide a solid attachment site for a prosthesis.

The technician then uses the stone model to construct an artificial tooth or multi-tooth prosthesis for eventual installation over the abutment or abutments in the patient's mouth. Bone anchorage of the implant body provides a solid attachment for the abutment, and hence secure anchorage for the installed prosthesis which may be cemented to the abutment or abutments, or otherwise secured if the prosthetic appliance is of the removable type.

Implant bodies have enjoyed significant success in restorative dentistry, but the inability of an oral surgeon to achieve routine ideal placement and alignment of the implant body in the jawbone creates a problem. Such ideal placement would position the longitudinal axis of the implant body, and hence the axis of the abutment, in a centralized location enabling the prosthesis to be placed in the desired position. The problem is aggravated where multiple implant bodies are installed to provide multipoint anchorage for a bridge or complete denture, and the abutment axes must be substantially parallel to enable prosthesis insertion. The problem of implant-body misalignment is typically present in a patient with eroded, weak or degenerated bone structure of a cross section which requires implant body insertion in a non-ideal orientation. These difficulties are discussed in greater detail in U.S. Pat. Nos. 5,052,929, 5,195,891, and 5,209,666, and, for brevity, the disclosures of these patents are incorporated herein by reference.

The present invention provides a solution to the problem of implant bodies which are necessarily placed in the jawbone in a non-ideal axial orientation. The invention enables a dental-laboratory technician to create a custom-shaped cast abutment which is angulated to correct the misalignment of the associated implant body, and which incorporates a precision metal base which mates perfectly with the implant body.

SUMMARY OF THE INVENTION

This invention relates to a system for making an abutment for attachment to a dental implant body, and which is custom shaped to correct for an imperfectly positioned implant body in a patient's jawbone.

The system includes a precision base made of a cast-to material such as gold or a gold alloy, the base preferably being configured to make a non-rotational mating fit on the implant body. The base has a cylindrical sleeve defining a first central axis, and having a bore extending there-through on the first axis.

The system further includes an abutment pattern made of a burn-out material, and having a mounting flange from which extends a post centered on a second central axis. A cylindrical bore extends through the pattern, and defines at the flange end of the pattern a cylindrical socket which mates with the base sleeve. In a first position, the pattern makes a rotational slip fit on the base sleeve, and in a second and fully seated position, the pattern and base are axially and rotationally fixed together.

The first and second axes are preferably angulated with respect to each other to provide correction for an imperfectly positioned implant body. The base sleeve preferably has a radially extending annular rib which makes an interference fit in the pattern socket to secure the pattern and base together in the second position.

The pattern shape may be augmented with dental wax, or reduced by grinding or similar machining to achieve a desired shape. The assembled pattern and base are then invested, and a metal replica of the pattern is cast on and bonded to the base to provide a custom abutment.

In an alternative form, both the base and abutment pattern are made of a burn-out plastic material, and the base and abutment of the final casting are integral.

BRIEF DESCRIPTION OF THE DRAWINGS

FIG. 1 is a exploded view of a dental implant body, an abutment pattern as mounted on a metal base, and an attachment screw;

FIG. 2 is a side view of the metal base;

FIG. 3 is an end view of the base on line 3—3 of FIG. 2;

FIG. 4 is a sectional side view of the base;

FIG. 5 is a side view of the abutment pattern;

FIG. 6 is an end view on line 6—6 of FIG. 5;

FIG. 7 is a sectional side view of the abutment pattern;

FIG. 8 is an end view on line 8—8 of FIG. 5;

DETAILED DESCRIPTION

Figure 9:
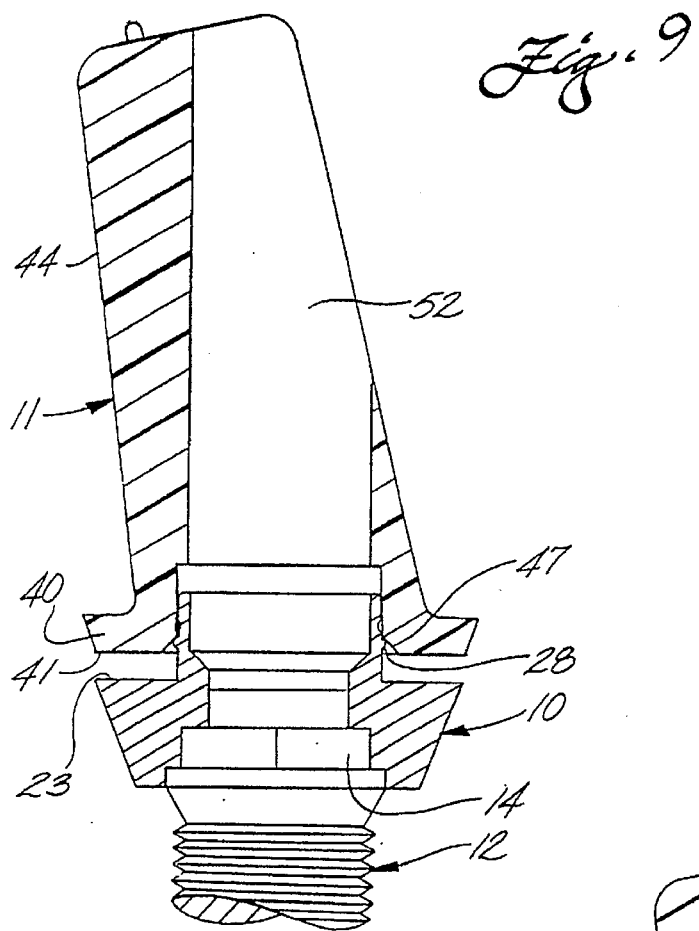
FIG. 9 is a sectional elevation of the base as secured to an implant analog, and the abutment pattern partially fitted on the base.

FIG. 1 is an exploded view showing a metal base 10 on which is rotatably mounted a plastic abutment pattern 11 shaped to make a mating fit on the upper end of an implant body 12. The implant body may be of any conventional and commercially available type, and the style illustrated is made by Branemark. This implant body has an elongated threaded shank 13, and a hexagonal head 14 dimensioned to mate with a hexagonal socket in base 10 as described below in detail. The implant body has a central longitudinal axis 15. A screw 16 with a tapered head 17 and a threaded shank 18 seats in base 10 with shank 18 secured in a mating threaded bore (not shown) extending from head 14 into shank 13 of the implant body.

Referring to FIGS. 2–4, base 10 has a body 20 which is rotationally symmetrical about a central axis 21. The body has an outer end face 22, an inner face 23 and an outer surface 24 which is inwardly conically tapered from the inner face to the outer end face.

A hollow mounting sleeve 26 extends axially from inner face 23, and the outer surface of the sleeve defines an annular groove 27, and an annular rib 28 positioned between the groove and inner face. The interior surface of hollow sleeve 26 defines a cylindrical lock-screw socket 30 having an inwardly tapered base 31 which terminates at a central cylindrical opening 32.

A circular recess 34 is centrally positioned in outer end face 22 of the base. A hexagonal socket 35 extends into the base from the inner end of recess 34, and the inner end of socket 35 terminates at a cylindrical opening 36 which extends to opening 32. As best seen in FIG. 2, recess 34 circumscribes hexagonal socket 35, and the socket in turn circumscribes opening 36.

The views of the base in FIGS. 2–4 are considerably enlarged, and typical dimensions for this part are 2.5-mm axial length, 5.5-mm diameter of inner face 23, 4.1-mm diameter of outer end face 24, and 2.9-mm outer diameter of sleeve 26. The base is made of a so-called "cast to" precious-metal alloy which is well known in dentistry. These alloys, typically gold alloys, are biocompatible, and readily accept and bond to other high-gold or palladium alloys which are eventually cast to the base to form an abutment structure attachable to the implant body.

FIGS. 5–8 are enlarged views of abutment pattern 12 which has a mounting flange 40 with an end surface 41, and a tapered outer surface 42, the flange being circularly symmetrical about a central axis 43. A tapered conical post 44 extends from the mounting flange, and the conical post has a central axis 45 which is angulated with respect to axis 42.

As shown in FIGS. 6–7, mounting flange 40 has a circular and inwardly tapered shallow recess 47 centered on axis 43. The recess extends to a cylindrical socket 48 (also centered on axis 43) having an inside diameter selected to receive mounting sleeve 26 of base 10 with a rotatable slip fit, and to make an interference fit over rib 28. The inner end of socket 48 terminates at an inwardly extending annular shoulder 49. The axial spacing of end surface 41 and shoulder 49 is selected to enable the entire mounting sleeve to seat within the socket.

A cylindrical bore 52 is centered on axis 43, and extends from shoulder 49 through the side and end surfaces of angulated post 44. The diameter of bore 52 is slightly larger than the outside diameter of screw head 17 so the screw can be inserted through the bore.

It is intended that the abutment pattern be available in a number of different angulations of conical-post axis 45 to flange central axis 43. The angulations can vary from zero to about 25 degrees in steps of about 5 degrees. A nonangulated conical post is useful with a correctly or nearly correctly aligned implant body, and the increasingly angulated posts accommodate increasingly misaligned implant body axes.

The abutment pattern is cast from a so-called "burn out" plastic or wax material which is familiar to dental technicians creating cast metal restorations using the lost-wax technique. A suitable plastic material is LEXAN 141R (in a clear 111 grade) available from General Electric. This material can be ground or otherwise machined to a desired customized shape.

In use, the dental technician removes the impression post from the implant analog embedded in the stone model of the patient's dental arch as described above, and seats base 10 on the accessible end of the implant analog. In the illustrated embodiment, seating is achieved by mating hexagonal head 14 of the implant analog with hexagonal socket 35 of the base to form a nonrotational connection between these parts.

The invention is useful with any form of connection between the implant body and base, and, for example, the illustrated "hex" connection can be reversed to provide a hexagonal socket in the implant analog, and a mating hexagonal extension on the base. When the base is seated on the implant analog, the parts are secured together by threading screw 16 into the implant analog until tapered head 17 of the screw seats on inwardly tapered base 31 of base screw socket 30.

An abutment pattern of the proper angulation to correct implant-body misalignment is then selected, and the pattern is partially fitted over mounting sleeve 26 of the base, with annular rib 28 in shallow recess 47 of the pattern base flange as shown in FIG. 9. In this position, the pattern is freely rotatable on the base, and the technician can adjust the rotational position to achieve desired alignment of conical post 44 with respect to the stone model.

Figure 10:
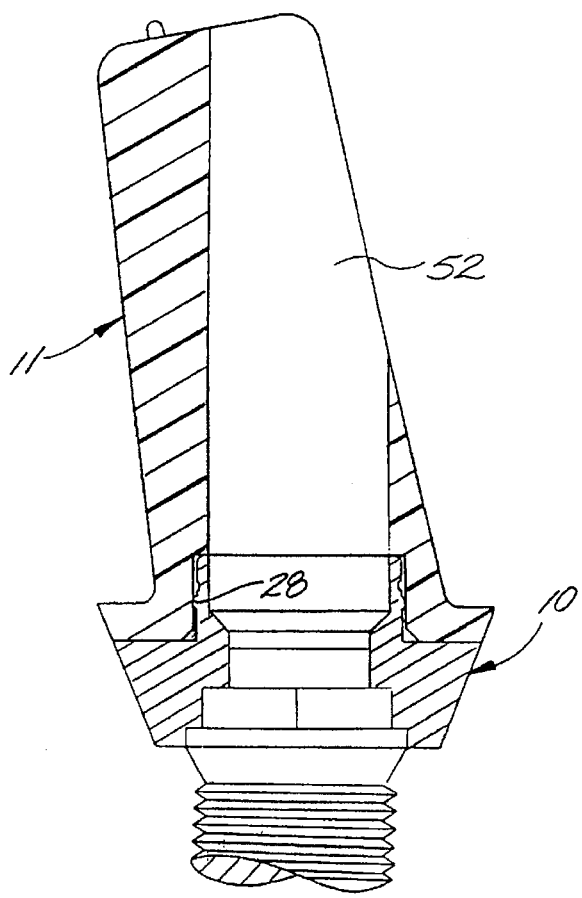
FIG. 10 is a view similar to FIG. 9, and showing the abutment pattern fully seated on the base.

When the conical post is correctly so aligned, the pattern is further pressed on the base sleeve to force annular rib 28 into cylindrical socket 48 into the position shown in FIG. 10. The base sleeve is then fully seated in socket 48, with mounting-flange end surface 41 in abutting contact with inner face 23 of the base. The interference fit (the annular rib typically has an outside diameter which is about 0.025-mm larger than the inside diameter of the socket) of the sleeve in the socket locks the two parts together in the desired rotational position, but it is possible to force these components to move rotationally should further adjustment be necessary.

The technician can then machine or add wax or plastic to the locked-in-position plastic pattern to achieve any shape adjustments which may be necessary. The pattern and base are then separated as a unit from the implant analog by removing screw 16, and the pattern and base are embedded in a conventional dental investment material in preparation for final casting.

The casting process is of the long-used "lost wax" technique in which the sprued investment is placed in a furnace, and heated to vaporize the burn-out-plastic or wax abutment pattern. Molten metal is then poured into the resulting precision cavity to exactly replicate the pattern in a final metal abutment which is metallurgically bonded to the "cast to" precious-metal base. The now-integrated base and abutment are then returned to the prosthodontist for installation in the patient's mouth and installation of the restorative prosthesis.

The embodiment described above is a preferred form of the invention because the use of cast-to metal enables production of a precision-machined base which accurately fits against and mates with the associated implant. An acceptable alternative embodiment of the invention, however, is to make both the base and abutment-pattern system components of burn-out plastic material of the type already described. These plastic components are manipulated and shaped as discussed above, but both components are vaporized during burn-out prior to the investment casting process, and replaced by an integral base and abutment composed of the selected casting metal. This embodiment is lower in cost (burn-out plastic being less expensive than cast-to precious-metal alloys), but is useful in applications where a slightly less-precise mating fit of base and implant is acceptable.

What is claimed is:

1. A system for making a model from which a customized dental abutment can be cast for attachment to an implant body embedded in a patient's jawbone, comprising:

a base made of a cast-to material, and configured to make a precision fit on the implant body, the base defining a sleeve with a first central axis;

an abutment pattern made of a burn-out material, and having a mounting flange centered on and extending radially from the first central axis when the base and pattern are mated, the pattern further having a post extending from the mounting flange, the post having a second central axis, the pattern having a bore extending through the mounting flange and post, the bore being centered on the first central axis, the flange end of the bore defining a cylindrical socket which makes a fit over at least a portion of the base sleeve; and engaging means cooperating between the base and pattern for supporting the pattern on the base in two different positions, the pattern having a first engaged position on the base sleeve in which the pattern is freely rotatable about the first central axis with respect to the base, and a second engaged position on the base sleeve in which the pattern and base sleeve are locked together.

2. The system defined in claim 1, and in which the first and second axes are angulated with respect to each other.

3. The system defined in claim 2, and in which angulation of the axes is in the range of about 25 degrees to slightly more than zero degrees.

4. The system defined in claim 2, and in which the base is made of a gold material, and the abutment pattern is made of plastic.

5. The system defined in claim 2, and in which the engaging means includes a radially outwardly extending annular rib on an outer surface of the base sleeve, the rib making a tight interference fit in the cylindrical socket when the base and pattern are in the second position.

6. The system defined in claim 2, and in which the base is adapted to make a non-rotational fit on the implant body.

7. A system for making a model from which a customized dental abutment can be cast for attachment to an implant body embedded in a patient's jawbone, comprising:

a base made of a burn-out material, and configured to make a precision fit on the implant body, the base defining a sleeve with a first central axis;

an abutment pattern made of a burn-out material, and having a mounting flange centered on and extending radially from the first central axis when the base and pattern are mated, the pattern further having a post extending from the mounting flange, the post having a second central axis, the pattern having a bore extending through the mounting flange and post, the bore being centered on the first central axis, the flange end of the bore defining a cylindrical socket which makes a fit over at least a portion of the base sleeve; and engaging means cooperating between the base and pattern for supporting the pattern on the base in two different positions, the pattern having a first engaged position on the base sleeve in which the pattern is freely rotatable about the first central axis with respect to the base, and a second engaged position on the base sleeve in which the pattern and base sleeve are locked together.

8. The system defined in claim 7, and in which the first and second axes are angulated with respect to each other.

9. The system defined in claim 8, and in which angulation of the axes is in the range of about 25 degrees to slightly more than zero degrees.

10. The system defined in claim 8, and in which the base and the abutment pattern are made of plastic.

11. The system defined in claim 8, and in which the engaging means includes a radially outwardly extending annular rib on an outer surface of the base sleeve, the rib making a tight interference fit in the cylindrical socket when the base and pattern are in the second position.

12. The system defined in claim 8, and in which the base is adapted to make a non-rotational fit on the implant body.

* * * * *